(12) United States Patent
Kim et al.

(10) Patent No.: US 12,283,264 B2
(45) Date of Patent: Apr. 22, 2025

(54) TARGETED MULTIFOCAL LENS FOR BIOLOGICAL SAMPLE PROCESSING AND RELATED METHODS

(71) Applicants: Triangle Biotechnology, Inc., Chapel Hill, NC (US); The University of North Carolina at Chapel Hill, Chapel Hill, NC (US)

(72) Inventors: Jinwook Kim, Chapel Hill, NC (US); Sandeep Kasoji, Durham, NC (US); Paul Dayton, Carrboro, NC (US); Joe McMahon, Chapel Hill, NC (US)

(73) Assignees: Triangle Biotechnology, Inc., Chapel Hill, NC (US); The University of North Carolina at Chapel Hill, Chapel Hill, NC (US)

( * ) Notice: Subject to any disclaimer, the term of this patent is extended or adjusted under 35 U.S.C. 154(b) by 430 days.

(21) Appl. No.: 17/640,073

(22) PCT Filed: Sep. 4, 2020

(86) PCT No.: PCT/US2020/049386
§ 371 (c)(1),
(2) Date: Mar. 3, 2022

(87) PCT Pub. No.: WO2021/046338
PCT Pub. Date: Mar. 11, 2021

(65) Prior Publication Data
US 2022/0328032 A1    Oct. 13, 2022

Related U.S. Application Data

(60) Provisional application No. 63/026,186, filed on May 18, 2020, provisional application No. 62/897,057, filed on Sep. 6, 2019.

(51) Int. Cl.
*G10K 11/30* (2006.01)
*B06B 1/06* (2006.01)
(Continued)

(52) U.S. Cl.
CPC ............ *G10K 11/30* (2013.01); *B06B 1/0622* (2013.01); *B06B 1/067* (2013.01); *C12M 47/06* (2013.01); *G01N 29/221* (2013.01); *B33Y 80/00* (2014.12)

(58) Field of Classification Search
CPC ....... G10K 11/30; B06B 1/0622; B06B 1/067; C12M 47/06; G01N 29/221; B33Y 80/00
(Continued)

(56) References Cited

U.S. PATENT DOCUMENTS

2002/0009015 A1* 1/2002 Laugharn, Jr. ........... B01J 19/10
366/108
2004/0264293 A1* 12/2004 Laugharn, Jr. ........ B01F 33/403
366/127
(Continued)

FOREIGN PATENT DOCUMENTS

WO    2007016605 A2    2/2007
WO    2009146140 A2    12/2009

OTHER PUBLICATIONS

Extended European Search Report corresponding to EP 20860773.9, Aug. 8, 2023, (8 pages).
(Continued)

*Primary Examiner* — John E Breene
*Assistant Examiner* — Rose M Miller
(74) *Attorney, Agent, or Firm* — Myers Bigel, P.A.

(57) ABSTRACT

A sonicator system for sonicating materials in a sample array includes a transducer layer configured to emit acoustic energy; and a multifocus acoustic lens layer configured to focus the acoustic energy from the transducer layer to the
(Continued)

sample array to thereby simultaneously sonicate materials in the sample array.

25 Claims, 11 Drawing Sheets (51) Int. Cl.
    *B33Y 80/00*     (2015.01)
    *C12M 1/00*     (2006.01)
    *G01N 29/22*     (2006.01)

(58) Field of Classification Search
    USPC .......................................................... 73/642
    See application file for complete search history.

(56) References Cited

U.S. PATENT DOCUMENTS

| | | | |
|---|---|---|---|
| 2009/0249866 A1* | 10/2009 | Vivek | ................ B41J 2/005 |
| | | | 73/64.48 |
| 2009/0249877 A1 | 10/2009 | Vivek et al. | |
| 2009/0254289 A1 | 10/2009 | Dadi et al. | |
| 2013/0244242 A1 | 9/2013 | Laugharn et al. | |
| 2017/0205318 A1 | 7/2017 | Matula et al. | |

OTHER PUBLICATIONS

International Search Report and Written Opinion for PT/US2020/049386 mailed Dec. 17, 2020, 11 pages.

* cited by examiner

FIG. 9A TARGET PATTERN

FIG. 9B CONVERGED PRESSURE AMPLITUDE ITERATION #30

FIG. 9C CONVERGED PRESSURE AMPLITUDE ITERATION #30

FIG. 9D 3-D-PRINTABLE (STL) HOLOGRAM LENS

TARGETED MULTIFOCAL LENS FOR BIOLOGICAL SAMPLE PROCESSING AND RELATED METHODS

RELATED APPLICATIONS

This application is a 35 U.S.C. § 371 national phase entry of International Application No. PCT/US2020/049386, filed Sep. 4, 2020, which claims priority to Application Ser. Nos. 62/897,054, filed Sep. 6, 2019, and 63/026,186, filed May 18, 2020, the disclosures of which are hereby incorporated by reference in their entireties.

STATEMENT OF GOVERNMENT SUPPORT

This invention was made with government support under Grant Number CA236177 awarded by the National Institutes of Health. The government has certain rights in the invention.

FIELD OF THE INVENTION

The present invention relates to sonicating microplates for sample processing, and in particular to multifocal lenses used for simultaneously sonicating samples in microplate wells.

BACKGROUND

Microplates are frequently used in molecular biology applications, particularly in sample processing (i.e., genomic DNA, chromatin, cells, tissues, etc.) for a range of high-throughput analytical techniques, including next-generation sequencing, chromatin immunoprecipitation, quantitative polymerase chain reaction, and the like. Focused ultrasound may be used for sample processing. However, the current technologies typically can only process one sample at a time, which prolongs processing time and significantly drives up the labor costs. Additionally, since processing occurs serially, a robotic system is used to raster scan the microplate across the single-focus transducer. This also drives up the instrument cost (>$150,000).

U.S. Patent Publication No. 2017/0205318 relates to an ultrasound system for shearing cellular material in which an array of transducer elements are positioned to align with sample wells in a microplate. Each transducer element produces energy that is focused towards a well of a microplate with sufficient acoustic pressure to cause inertial cavitation.

SUMMARY OF EMBODIMENTS OF THE INVENTION

In some embodiments, a sonicator system for sonicating materials in a sample array includes a transducer layer configured to emit acoustic energy; and a multifocus acoustic lens layer configured to focus the acoustic energy from the transducer layer to sample wells of the microplate to thereby simultaneously sonicate materials in the sample array.

In some embodiments, the transducer layer comprises a single, substantially homogenous acoustic source and the multifocus acoustic lens layer is configured to focus acoustic energy from the single, substantially uniform acoustic source to one or more samples in the sample array.

In some embodiments, the transducer layer comprises a plurality of transducers that are mechanically connected to thereby form a substantially homogenous acoustic source.

In some embodiments, the transducer layer comprises a plurality of piezoelectric transducers that are mechanically connected to thereby form a substantially homogenous acoustic source.

In some embodiments, the transducer layer comprises a plurality of Langevin transducers that are mechanically connected to thereby form a substantially homogenous acoustic source.

In some embodiments, the multifocus acoustic lens comprises an acoustic kinoform lens.

In some embodiments, the multifocus lens is formed by holography techniques.

In some embodiments, the multifocus lens comprises a single, unitary member.

In some embodiments, the multifocus lens comprises a 3D printed acoustic lens.

In some embodiments, the multifocus lens is formed of resin, metal, polymer material.

In some embodiments, the multifocus lens is configured to focus acoustic energy from the transducer layer to a plurality of focal points, each one of the plurality of focal points corresponding to the plurality of sample wells.

In some embodiments, the multifocus lens is configured to focus acoustic energy from the transducer layer to a single, substantially homogenous acoustic field that sonicates the plurality of sample wells.

In some embodiments, the multifocus lens is configured to focus acoustic energy from the transducer layer to one or more regions that are configured to sonicate the plurality of sample wells.

In some embodiments, the multifocus lens is configured to focus the acoustic energy from the transducer to an acoustic beam pattern that sonicates the plurality of sample wells.

In some embodiments, the lens is configured to focus the acoustic energy of the transducer layer to provide an acoustic field for sonicating the plurality of sample wells by modifying the phase of the transducer layer.

In some embodiments, the samples are biological samples, chemical samples or combinations thereof.

In some embodiments, the lens is configured to focus the acoustic energy so as to shear nucleic acids, proteins, chromatin and/or intracellular materials.

In some embodiments, the lens is configured to focus the acoustic energy for the lysis of cells, tissue, and/or biofilm for the extraction or release of intracellular or extracellular materials such as proteins, metabolites, nucleic acids and chromatin.

In some embodiments, the lens is configured to focus the acoustic energy for in-vitro sonoporation of cells and tissues for the purposes of transfection, drug delivery, or applications requiring a transient permeability of cellular or tissue membrane.

In some embodiments, the sonicator system comprises an acoustic mating layer to acoustically couple the transducer layer to the lens.

In some embodiments, methods of sonicating a plurality of samples in samples wells of a microplate are provided. The methods may include emitting acoustic energy from a transducer layer; and focusing acoustic energy from the transducer layer to a plurality of focal points or regions with a multifocus acoustic lens to thereby sonicate the plurality of samples in the sample wells.

In some embodiments, the sample array comprises a microplate.

In some embodiments, the sample array comprises glass or plastic tubes, containing the sample to be sonicated, and positioned in an array.

In some embodiments, the multifocus acoustic lens layer is not cylindrically focused.

In some embodiments, the multifocus acoustic lens layer produces greater than eight independent acoustic foci.

In some embodiments, the multifocus acoustic lens layer produces greater than 24 independent acoustic foci.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 1A is a side schematic view of still another sonicator system for sonicating a sample in a microplate according to some embodiments.

DETAILED DESCRIPTION OF EMBODIMENTS OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

As used herein, an acoustic, kinoform lens is a multifocus acoustic lens that may be used to focus acoustic energy to various shapes.

Holography techniques as used herein refer to techniques used to form an acoustic lens to achieve a desired acoustic output. If the amplitude and/or phase of an acoustic field is varied across the wave front, it is possible to project an acoustic "image" or transmission hologram. An acoustic hologram is formed (structured and/or shaped) such that it matches the wave-front shape of the primary ultrasound wave and the holographic ultrasound field to be obtained. For example, the structure data can be obtained by solving the inverse diffraction problem in dependency on the holographic ultrasound field to be created and the radial phase and amplitude distribution of the primary ultrasound wave from a transducer source. Alternatively, the transmission hologram can be formed as a phase hologram formed by a numerical approximation using an error-reduction algorithm, such as the Gerchberg-Saxton algorithm, in dependency on the holographic ultrasound field to be created and the radial phase and amplitude distribution of the primary ultrasound wave.

A hologram acoustic lens can be made using the calculated hologram phase structure by the use of a rapid prototyping method, such as a 3D printing method. This has advantages in terms of high resolution (e.g. 50 µm), high-speed and cheap manufacturing, and capability of digital material combinations.

A sonicator system for sonicating materials in a sample well of a microplate is provided. In some embodiments, the sonication is useful for shearing biological materials in a sample well of a microplate.

A "microplate" includes any suitable vessels for use with a sonicator that focuses an acoustic field in a specific region, such as an array. Examples of microplates include, but are not limited to, 96- and 384-well PCR plates, and 6-, 12-, 24-, and 96-microtiter plates. It should be understood that other sample arrays may be used, including tubes or vials arranged in an array. Examples of arrays include a grid, linear or circular arrays.

As illustrated in FIGS. 1A-1C and FIG. 2, a sonicator system 100 is illustrated. The sonicator system 100 includes a transducer layer 110 having transducers 112 configured to emit acoustic energy, and a multifocus acoustic lens layer 120 configured to focus the acoustic energy from the transducer layer 110. The system 100 further includes a conductive acoustic mating or matching layer 130, conductive film 140, a low density backing material 150, a high voltage power source 160, and a receptacle 170, which typically is used to hold a water bath. A microplate 200 includes a plurality of sample wells 210 and is positioned in the receptacle 170 on top of the water bath.

Figure 1A:
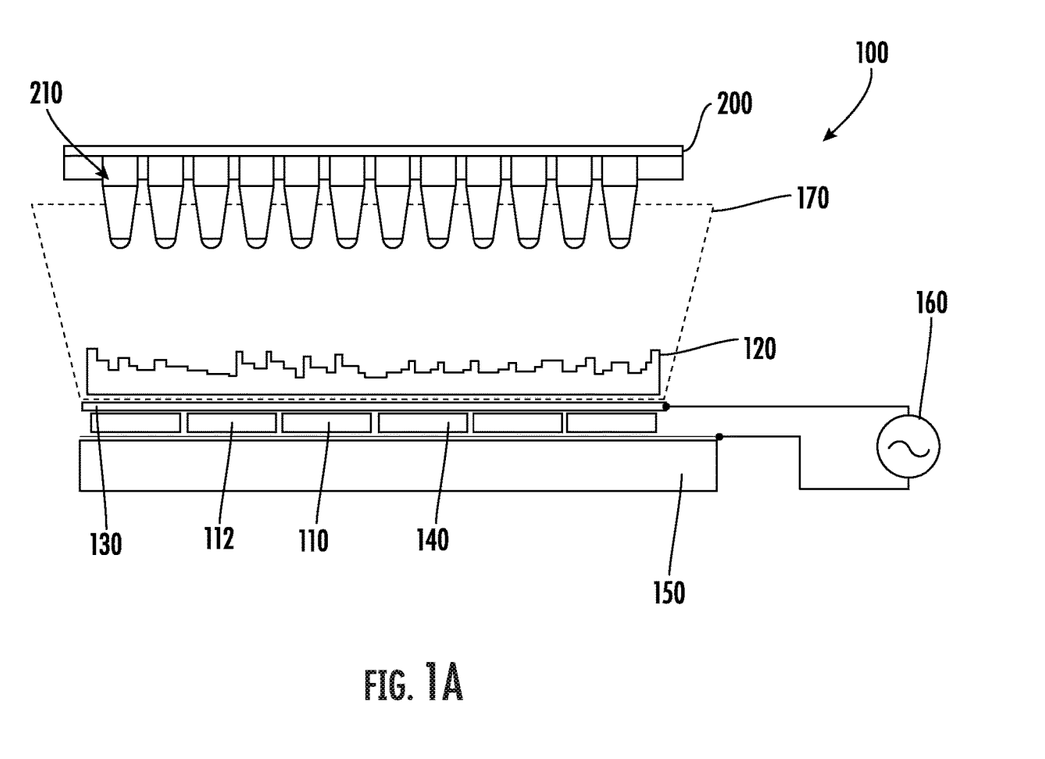
FIG. 1A is a side schematic view of a sonicator system for sonicating a sample in a microplate according to some embodiments.
Figure 1B:
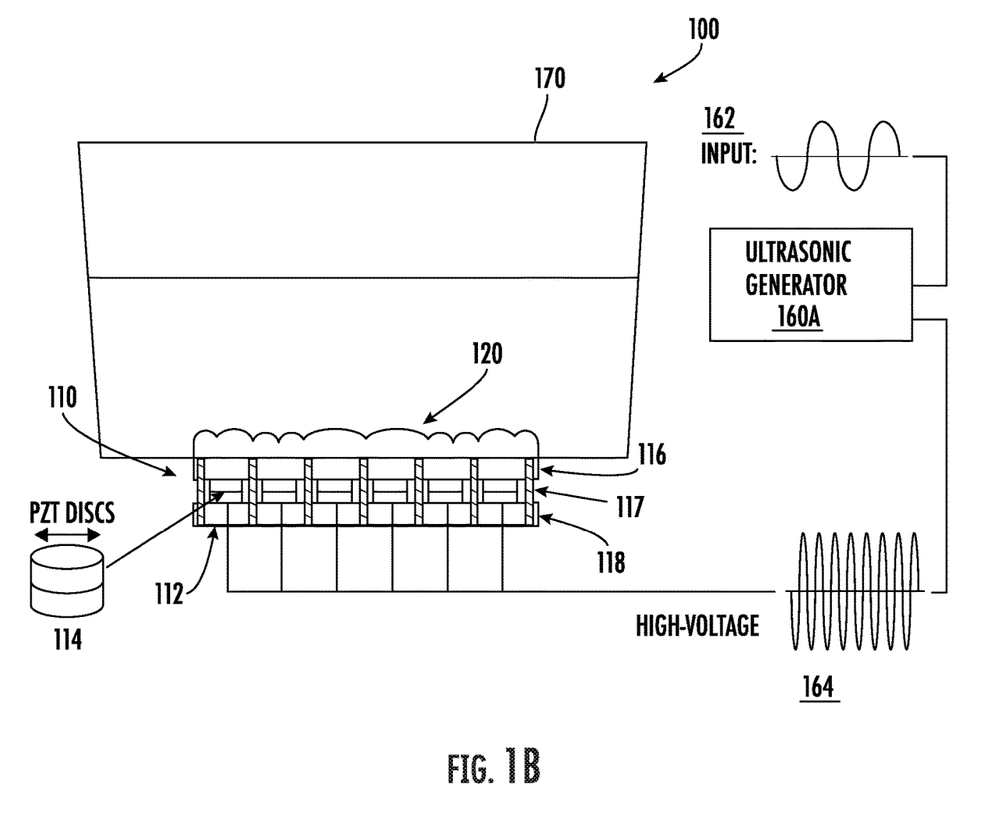
FIG. 1B is side view of another sonicator system according to some embodiments.
Figure 1C:
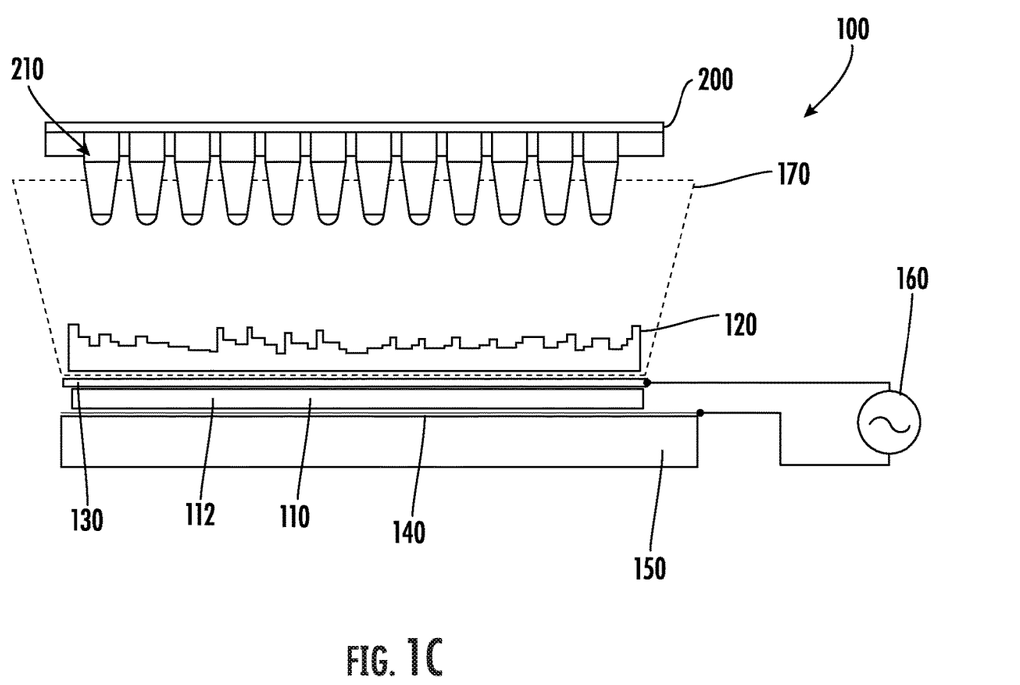
Figure 2:
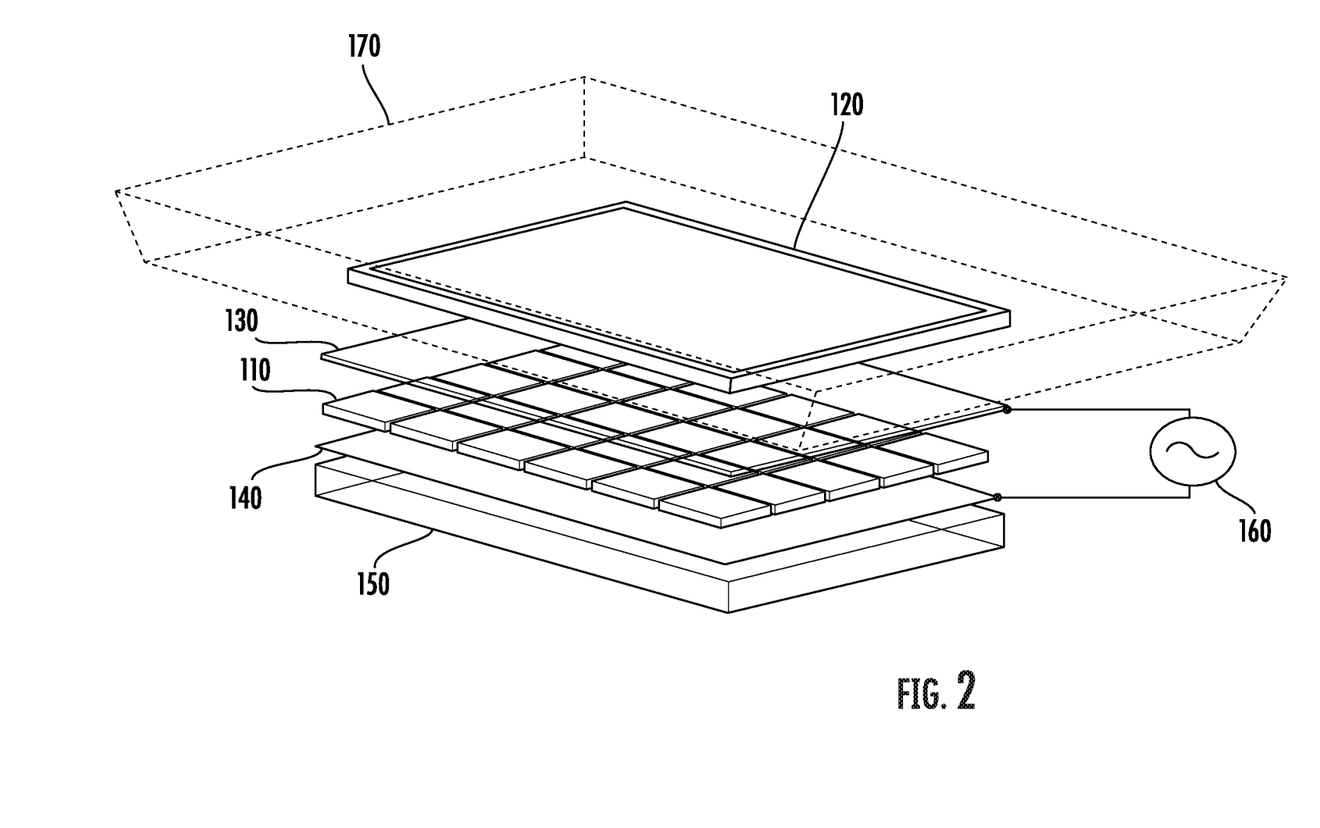
FIG. 2 is an exploded view of the sonicator system of FIG. 1.

As shown in FIG. 1B, the power source can include an ultrasonic generator 160A with an input 162 (typically about 100-250V) that delivers a high voltage signal 164 (typically 100-500 kHz) to the transducer layer 110. As shown, the transducer layer 110 includes transducers 112 that have a piezoelectric disk sandwiched between head mass 116 and a tail mass 118 and are mechanically mounted together with bolts 117. The transducers 112 are Langevin (sandwich-type) transducers; however, it should be understood that any suitable transducer(s) may be used. As shown in FIG. 1C, the transducer layer 110 may be a single transducer 112A.

As illustrated, the transducer layer 110 comprises a single, substantially homogenous acoustic source and the multifocus acoustic lens layer is configured to focus acoustic energy from the single, substantially uniform acoustic source to one or more sample wells of the microplate.

Although the transducer layer 110 is illustrated as a transducer array, the acoustic field from the transducer may approximate a single, acoustic source due to close spacing of the transducers 112 and the mechanically bolting together of the transducers. It sound be understood that a single source transducer (or an array of transducers acting together as a single source transducer) generates a heterogeneous beam adjacent to the front of the radiation aperture, and the acoustic field variation can be higher than 30%. It is estimated that an input pressure field has the −6 dB beam area larger than 70% of the radiation surface area. The heterogeneous nature of the beam is taken into account by the kinoform lens. In some embodiments, a single acoustic transducer, which may be in an array of transducers, emits an acoustic field that is divided into two or more focal points or regions. In some embodiments, the acoustic field that is generated by multiple acoustic transducers in an array of transducers is focused to provide an excitation region at a distance from the transducers. The excitation region can be continuous at a distanced from the transducer(s) and may be generated by two or more acoustic transducers.

In this configuration, the multifocus acoustic lens layer 120 focuses acoustic energy from the transducer layer 110 to the sample wells. As illustrated, the multifocus lens comprises a single, unitary member, i.e., without seams or breaks and formed of the same material throughout. The multifocus acoustic lens layer 120 may be a kinoform lens made by holography techniques to emit acoustic energy at a frequency and energy that is sufficient to sonicate sample materials in the wells 210 to thereby simultaneously sonicate biological materials in the sample wells. Stated otherwise, the kinoform lens may be calculated based on a desired sonication pattern using holography techniques. For example, an angular spectrum approach (ASA) technique may be used to theoretically calculate the configuration of the lens, and the lens may be formed by 3D printing, although injection molding, machining/during or other forms of manufacturing using materials including polymers (resins), metals, etc. may be used. For example, suitable 3-D printing polymers, such as a photopolymer resin with tensile modulus of 4.1 GPa (FLRGWH01, Formlabs), can be used. The lens may be bonded to an acoustic window or acoustic matching layer 130 using an acoustically compatible bonding agent or can be a fixture at a specific distance away from the acoustic window or matching layer 130 so that the acoustically compatible coupling media allows for acoustic energy transmission. However, in some embodiments, the surface profile can be shaped directly on the acoustic window or matching layer 130, e.g., a complex surface profile of the lens may be machined directly into an acoustic horn, thus not requiring a bonding agent used to attached a separate lens.

Multifocus lenses according to embodiments of the current invention may be configured to focus acoustic energy from the transducer layer to a plurality of focal points or regions, each one of the plurality of focal points corresponding to the plurality of sample wells. Various patterns of focal points or focal regions may be used. For example, the multifocus lens may be configured to focus acoustic energy from the transducer layer to a single, substantially homogenous acoustic field that sonicates the plurality of sample wells, e.g., at the distance of the sample wells. The multifocus lens may be configured to focus acoustic energy from the transducer layer to one or more regions that are configured to sonicate the plurality of sample wells. The multifocus lens may be configured to focus the acoustic energy from the transducer to an acoustic beam pattern that sonicates the plurality of sample wells. The lens may be configured to focus the acoustic energy of the transducer layer to provide an acoustic field for sonicating the plurality of sample wells by modifying the phase of the transducer layer.

Figure 3:
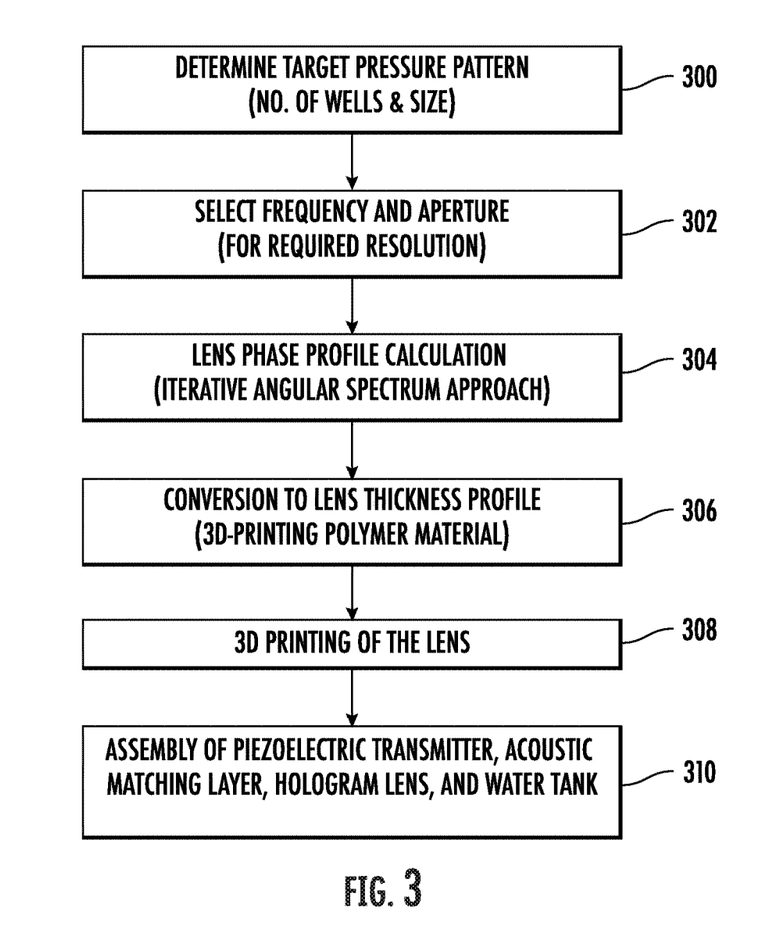
FIG. 3 is a flowchart showing methods of making an acoustic lens according to some embodiments.

An example technique for manufacturing a multifocus lens is shown in FIG. 3. The target pressure pattern is determined in Block 300, e.g., including a number of wells and the size of the sonication pattern, although stripes or other regional pressure patterns may be used as discussed herein. The frequency and aperture for the required resolution is selected at Block 302. The lens phase profile is calculated at Block 304 based on the target pressure pattern desired and the frequency and aperture selected. The calculated lens phase profile is converted to a lens thickness profile based on a selected 3D printing material at Block 306. The lens is printed at Block 308, for example, by 3D printing. A piezoelectric transmitter, acoustic matching layer, hologram lens and water tank are assembled for sonicating a sample at Block 310.

Figure 4:
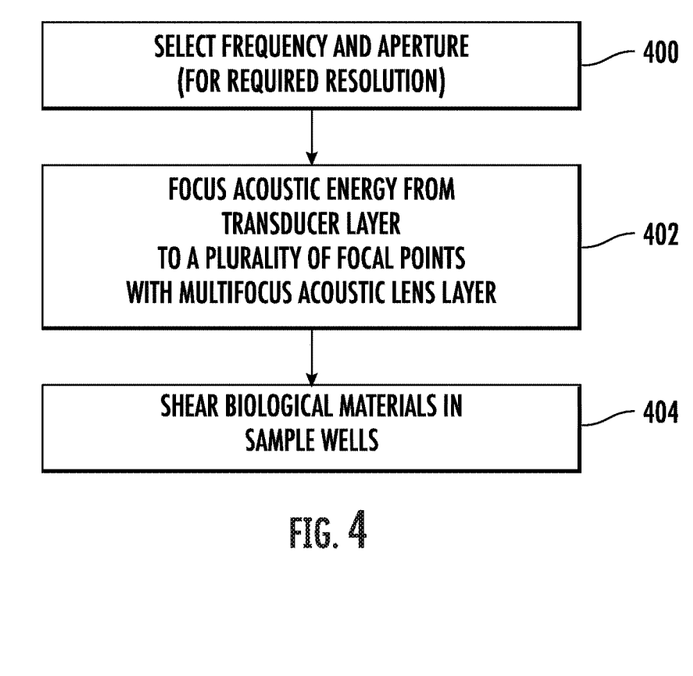
FIG. 4 is a flowchart showing methods of sonicating materials in sample wells according to some embodiments.
Figure 5:
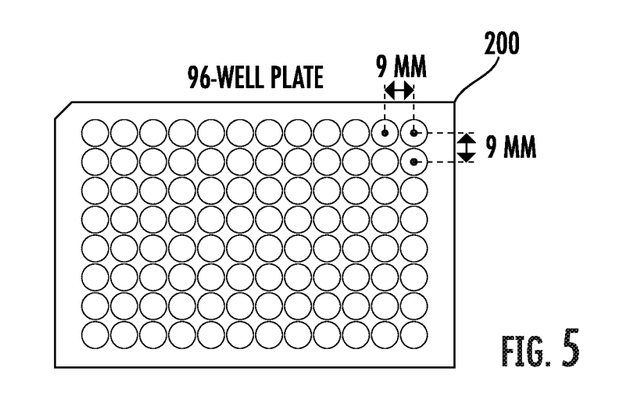
FIG. 5 is a top view of a microplate with sample wells according to some embodiments.
Figure 6:
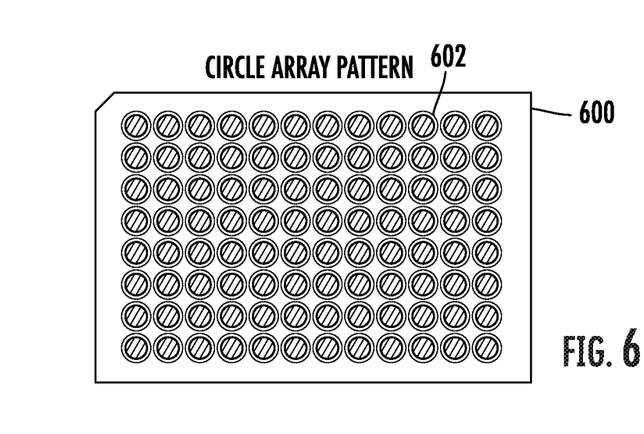
FIG. 6 is a top view of a circle array acoustic pattern generated by an acoustic lens of a sonicator system at the microplate according to some embodiments.
Figure 7:
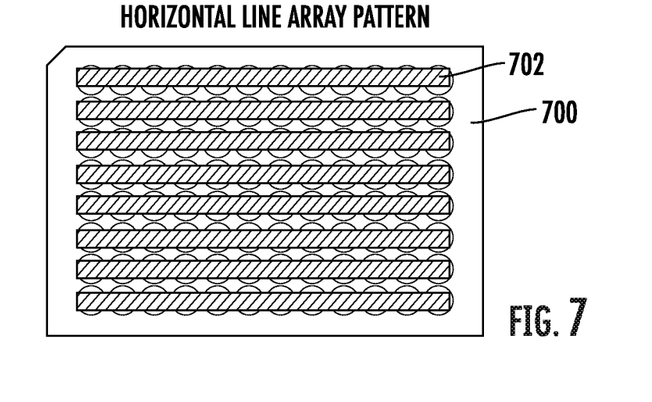
FIG. 7 is a horizontal line array pattern generated by an acoustic lens of a sonicator system at the microplate according to some embodiments.
Figure 8:
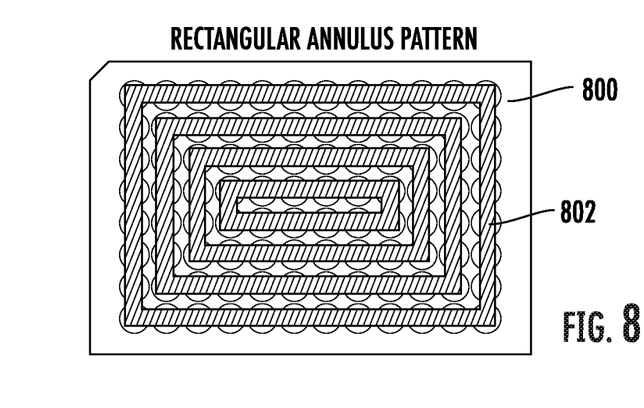
FIG. 8 is a rectangular annulus pattern generated by an acoustic lens of a sonicator system at the microplate according to some embodiments.

As illustrated in FIG. 4, acoustic energy is emitted from the transducer layer at Block 400. Acoustic energy is focused from the transducer layer to a plurality of focal points with the multifocus acoustic lens at Block 402. The samples are sonicated in the sample wells at Block 404.

Various non-limiting examples of acoustic focal patterns are discussed with reference to FIGS. 5-8.

Figure 9A:
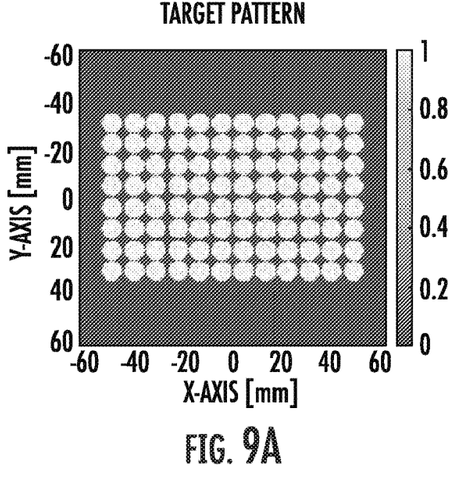
FIG. 9A is an image of a target pattern showing a circle array for an acoustic lens according to some embodiments.
Figure 9B:
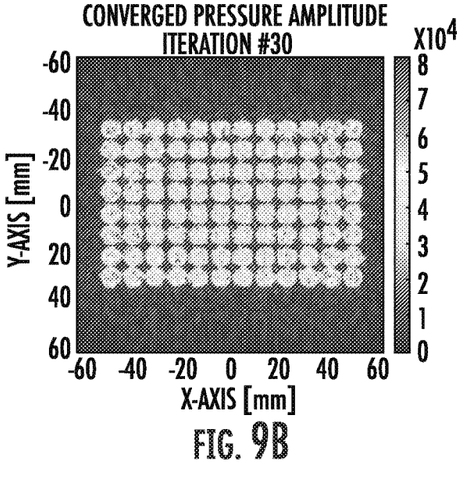
FIG. 9B is an image of a converged pressure amplitude simulated for the target pattern of FIG. 9A.
Figure 9C:
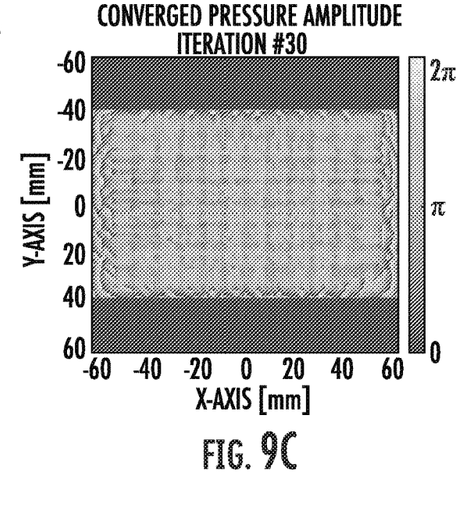
FIG. 9C is an image of a phase profile of a hologram lens calculated for the converged pressure amplitude of FIG. 9B.
Figure 9D:
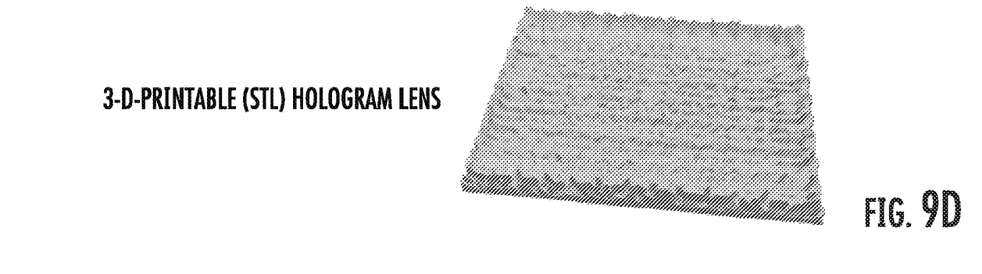
FIG. 9D is a hologram lens that may be represented as an STL file for 3D printing based on the phase profile of FIG. 9C.

As illustrated in FIGS. 9A-9D, a target pattern showing a circle array for an acoustic lens is shown. Each circle on the array may correspond to a sample well of a microplate and be focused at a suitable distance from the transducer layer to sonicate a sample in the sample well. FIG. 9B is an image of a converged pressure amplitude simulated for the target pattern of FIG. 9A. FIG. 9C is an image of a phase profile of a hologram lens calculated for the converged pressure amplitude of FIG. 9B. FIG. 9D is a hologram lens that may be represented as an STL file for 3D printing based on the phase profile of FIG. 9C.

Figure 10A:
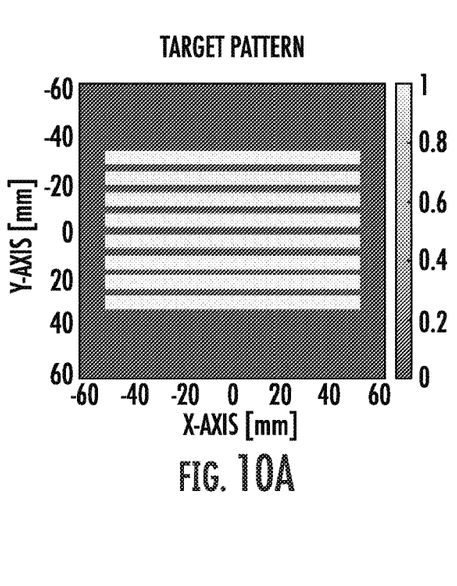
FIG. 10A is an image of a target pattern showing a horizontal line array for an acoustic lens according to some embodiments.
Figure 10B:
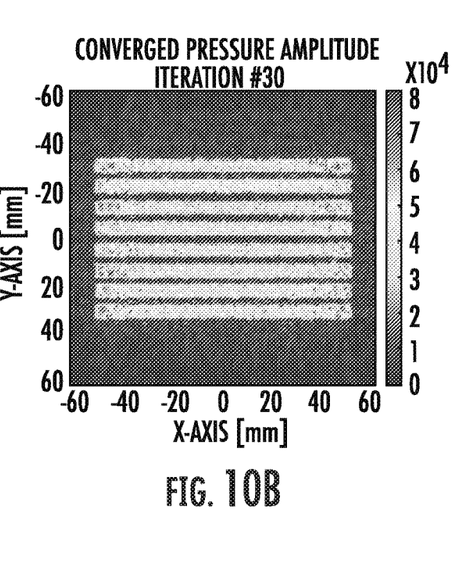
FIG. 10B is an image of a converged pressure amplitude simulated for the target pattern of FIG. 10A.
Figure 10C:
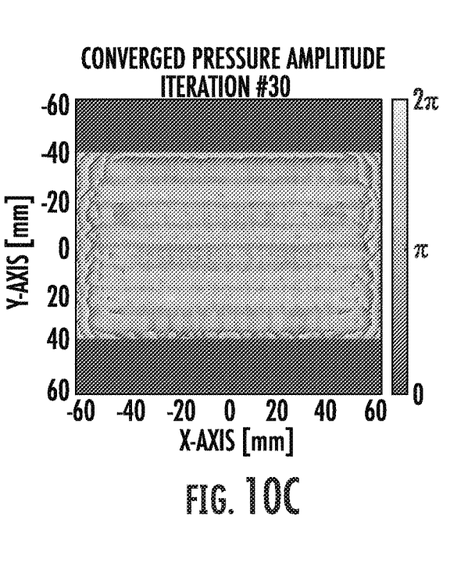
FIG. 10C is an image of a phase profile of a hologram lens calculated for the converged pressure amplitude of FIG. 10B.
Figure 10D:
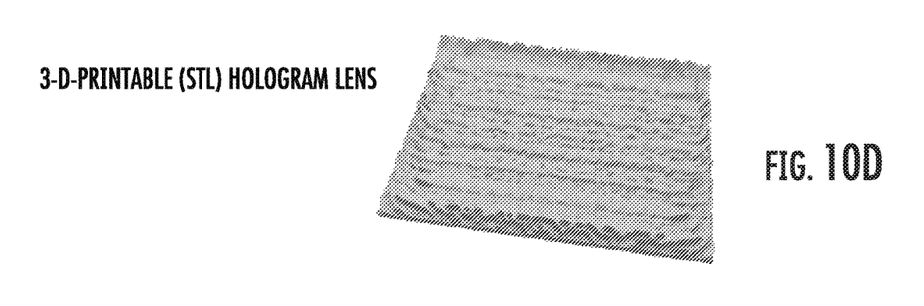
FIG. 10D is a hologram lens that may be represented as an STL file for 3D printing based on the phase profile of FIG. 10C.

As illustrated in FIGS. 10A-10D, a target pattern of a horizontal line array for an acoustic lens may be used. Each line of the horizontal line array may correspond to a plurality of sample wells of a microplate and be focused at a suitable distance from the transducer layer to sonicate a sample in the sample well. FIG. 10B is an image of a converged pressure amplitude simulated for the target pattern of FIG. 10A. FIG. 10C is an image of a phase profile of a hologram lens calculated for the converged pressure amplitude of FIG. 10B. FIG. 10D is a hologram lens that may be represented as an STL file for 3D printing based on the phase profile of FIG. 10C.

Figure 11A:
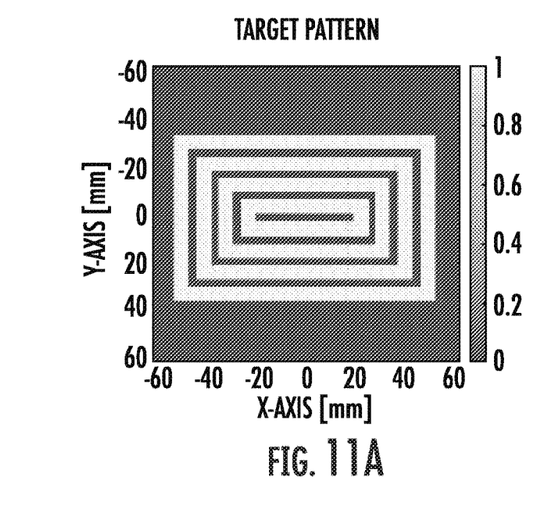
FIG. 11A is an image of a target pattern showing a rectangular annulus pattern for an acoustic lens according to some embodiments.
Figure 11B:
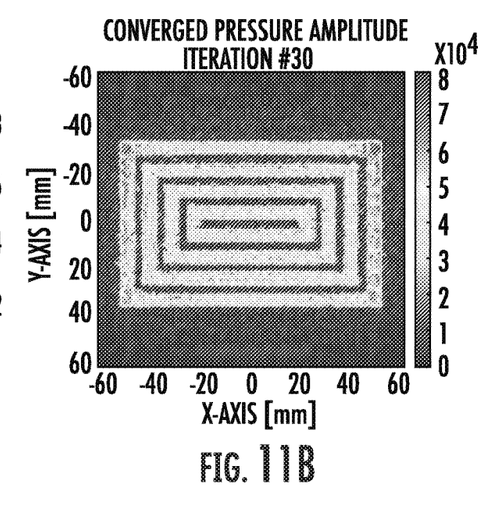
FIG. 11B is an image of a converged pressure amplitude simulated for the target pattern of FIG. 11A.
Figure 11C:
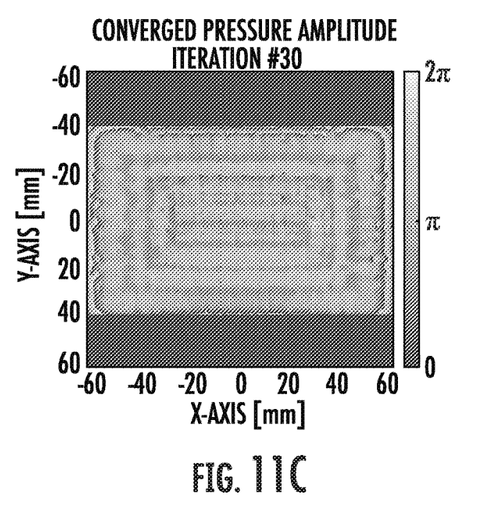
FIG. 11C is an image of a phase profile of a hologram lens calculated for the converged pressure amplitude of FIG. 11B.
Figure 11D:
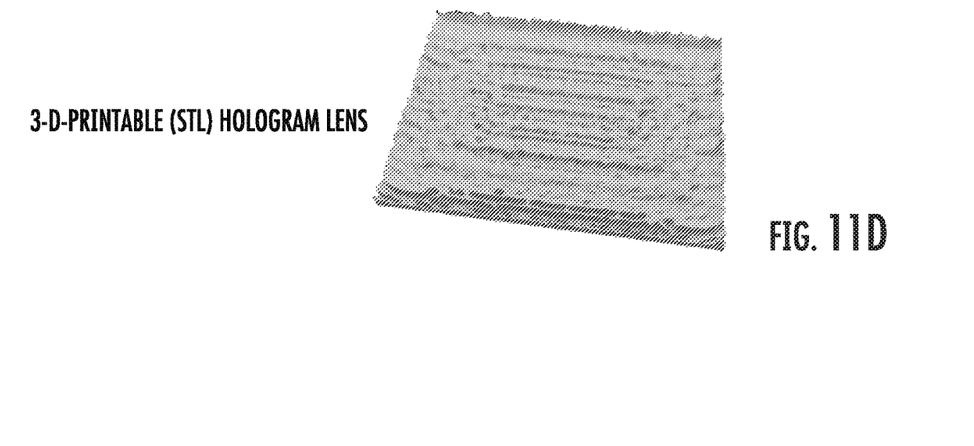
FIG. 11D is a hologram lens that may be represented as an STL file for 3D printing based on the phase profile of FIG. 11C.

As illustrated in FIGS. 11A-11D, a target pattern showing a rectangular annulus pattern for an acoustic lens may be used. The sonicated regions of the rectangular annulus pattern may correspond to regions that include sample wells of a microplate and may be focused at a suitable distance from the transducer layer to sonicate a sample in the sample well. FIG. 11B is an image of a converged pressure amplitude simulated for the target pattern of FIG. 11A. FIG. 11C is an image of a phase profile of a hologram lens calculated for the converged pressure amplitude of FIG. 11B. FIG. 11D is a hologram lens that may be represented as an STL file for 3D printing based on the phase profile of FIG. 11C.

Figure 12A:
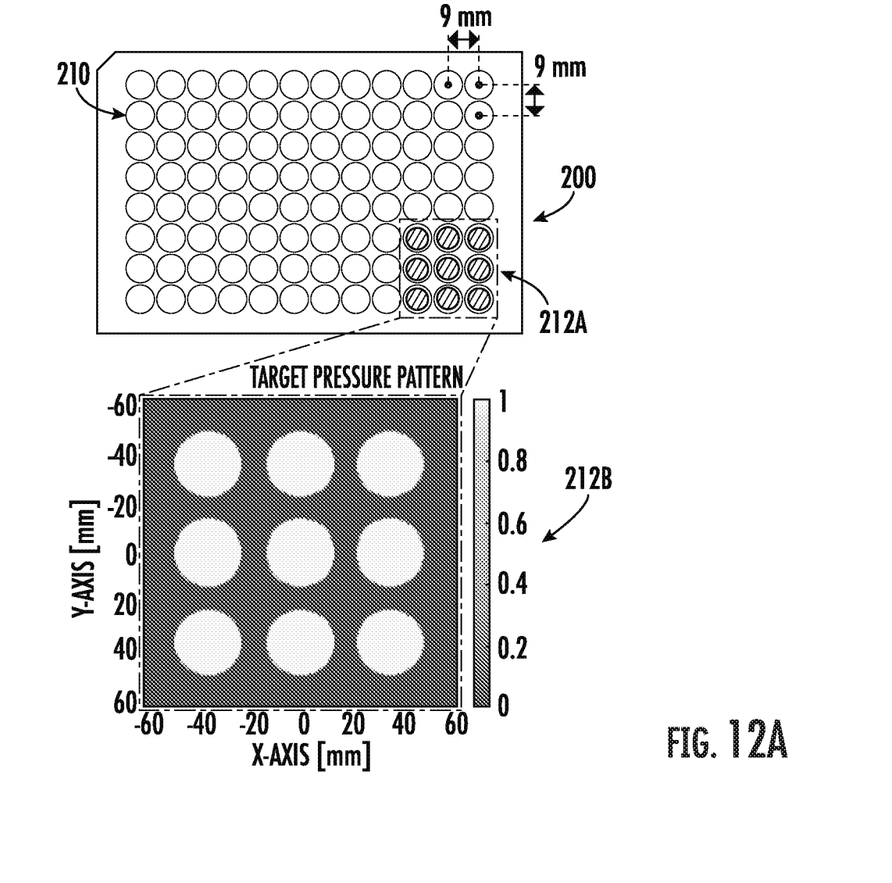
FIG. 12A is a top view of a microplate sample array and an expanded view illustrating a corresponding target pressure pattern for a portion of the array according to some embodiments.
Figure 12B:
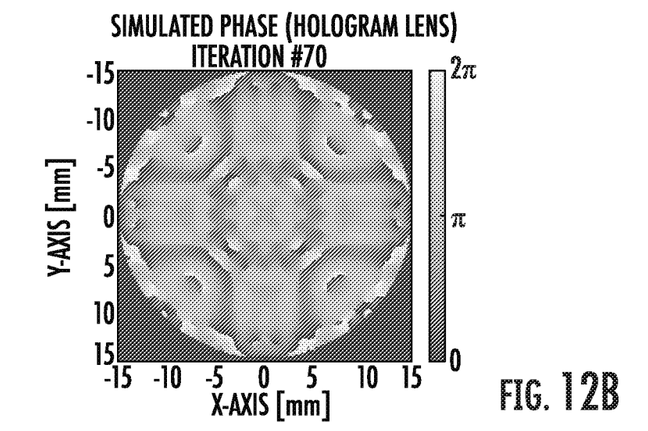
FIG. 12B is an image of a simulated phase holographic lens calculated based on the target pressure pattern for the portion of the array shown in FIG. 12A.
Figure 12C:
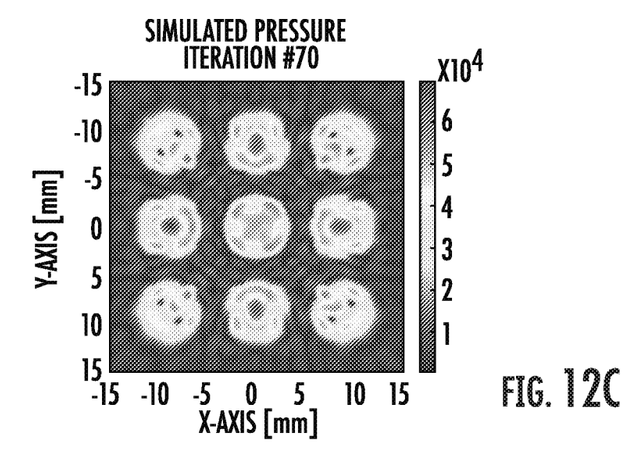
FIG. 12C is an image of a simulated pressure of the holographic lens of FIG. 12B.
Figure 12D:
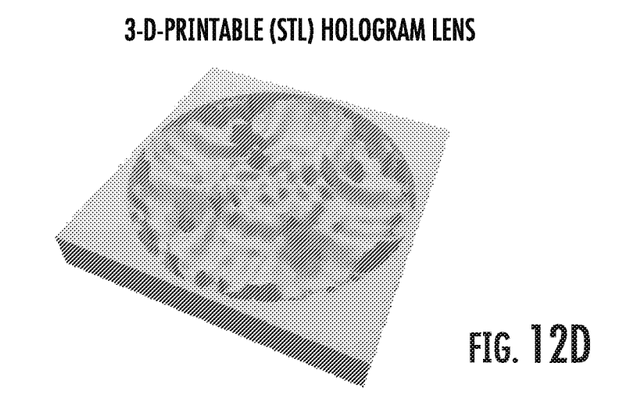
FIG. 12D is a perspective view of a hologram lens that may be represented as an STL file for 3D printing based on the simulated phase of FIG. 12B.

FIGS. 12A-12E illustrate a calculation for sonicating a microplate sample array with a circle array. A calculation for a single circle of a circle array is shown. In particular, FIG. 12A is a top view of a microplate sample array 200 of sample wells 210. A subset 212A of sample wells 210 is selected, and an expanded view illustrating a corresponding target pressure pattern for a portion of the array 212B is shown according to some embodiments. FIG. 12B is an image of a simulated phase holographic lens calculated based on the target pressure pattern for the portion of the array shown in FIG. 12A. FIG. 12C is an image of a simulated pressure of the holographic lens of FIG. 12B. FIG. 12D is a perspective view of a hologram lens that may be represented as an STL file for 3D printing based on the simulated phase of FIG.

Figure 12E:
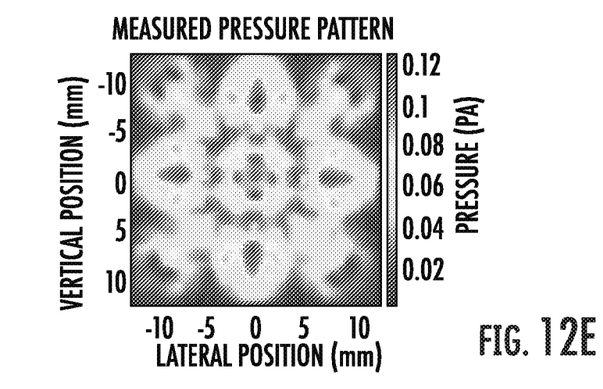
FIG. 12E is an image of a measure pressure pattern based on the lens of FIG. 12D.

12B. FIG. 12E is an image of a measure pressure pattern based on the lens of FIG. 12D.

The samples may be biological samples, chemical samples or combinations thereof. The lens may be configured to focus the acoustic energy so as to shear nucleic acids, proteins, chromatin and/or intracellular materials. The lens may be configured to focus the acoustic energy for the lysis of cells, tissue, and/or biofilm for the extraction or release of intracellular or extracellular materials such as proteins, metabolites, nucleic acids and chromatin. The lens may be configured to focus the acoustic energy for in-vitro sonoporation of cells and tissues for the purposes of transfection, drug delivery, or applications requiring a transient permeability of cellular or tissue membrane. Biological samples include, but are not limited to, source organisms of cells, tissues or biofilms of samples, and eukaryotic (vertebrate, invertebrate, and plant samples), microbial, and viral samples. In some embodiments, sonication systems may be used to create emulsions. Applications include, but are not limited to, high throughput extraction of materials for pathogen diagnostics, as well as the extraction of metabolites from plant specimens for drug analysis.

Lenses according to embodiments of the current invention may be used for in-vitro or in-vivo sonoporation. Organic or non-organic materials may be used as samples in the sample wells.

Complex beam profiles may be produced by applying time delays to a 1 or 2D array of ultrasound transducer elements.

The ultrasound frequencies generally applied by the transducer, in some embodiments, may be 10 kHz-2 MHz, 2 MHz-10 MHz, or 10 MHz-50 MHz.

Although any suitable sample or sample well configuration may be used, lenses according to some embodiments may be optimized for 24-96 samples or for 96-384 samples.

Moreover, the number of acoustic foci may be greater than the number of acoustic sources. For example, as illustrated in FIGS. 12A-12E, a single acoustic source may be used to provide nine or more target pressure foci in the subset 212A of sample wells 210. In some embodiments, a single acoustic source may be used to provide target pressure foci in the entire region of the microplate sample wells 210. Lenses may be used to produce an acoustic field of any suitable shape, such as rectangles, circles, or triangles, and in a range of sizes, such as from 1 $mm^2$ to 4000 $mm^2$, and the energy at any given point is above a threshold such that all samples get a minimum amount of energy or where the acoustic energy is distributed across the samples such that the samples are completely processed within a set time. The focus/foci or distance to the desired acoustic field can range any where from 1 mm to 1 m. The focus or focal zone is defined as the convergence point of acoustic energy or the narrowest region of the acoustic beam. Example pressures at the desired acoustic field/focus/foci can range from 100 Pa to 500 MPa, from 500 Pa to 5 MPa, or from 5 MPa to 50 MPa.

In some embodiments, an array of foci may be produced from just a single acoustic source. Alternatively, the lens can produce a single, homogenous acoustic field that encompasses the entire multiwall plate (e.g., a 96-well plate), or a portion of a plate or various focal regions may be generated. The potential advantages of this approach are that instrument cost and complexity are dramatically reduced, and the ability to process an entire microplate in parallel is a significant advancement in sample processing throughput (i.e., 2+ hours vs. 10-15 minutes for 96 samples).

The foregoing is illustrative of the present invention and is not to be construed as limiting thereof. Although a few example embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A sonicator system for sonicating materials in a sample array, the system comprising:
   a transducer layer configured to emit acoustic energy; and
   a multifocus acoustic lens layer configured to focus the acoustic energy from the transducer layer to the sample array to thereby simultaneously sonicate materials in the sample array, wherein the multifocus lens layer is formed by holography techniques.

2. The sonicator system of claim 1, wherein the transducer layer comprises a single, homogenous acoustic source and the multifocus acoustic lens layer is configured to focus acoustic energy from the single, substantially uniform acoustic source to one or more samples in the sample array.

3. The sonicator system of claim 1, wherein the transducer layer comprises a plurality of transducers that are mechanically connected to thereby form a substantially homogenous acoustic source.

4. The sonicator system of claim 1, wherein the transducer layer comprises a plurality of piezoelectric transducers that are mechanically connected to thereby form a substantially homogenous acoustic source.

5. The sonicator system of claim 1, wherein the transducer layer comprises a plurality of Langevin transducers that are mechanically connected to thereby form a substantially homogenous acoustic source.

6. The sonicator system of claim 1, wherein the multifocus acoustic lens layer comprises an acoustic kinoform lens.

7. The sonicator system of claim 1, wherein the multifocus lens layer comprises a single, unitary member.

8. The sonicator system of claim 1, wherein the multifocus lens layer is formed of resin, metal, or polymer material.

9. The sonicator system of claim 1, wherein the multifocus lens layer is configured to focus acoustic energy from the transducer layer to a plurality of focal points, each one of the plurality of focal points corresponding to the plurality of sample wells.

10. The sonicator system of claim 1, wherein the multifocus lens layer is configured to focus acoustic energy from the transducer layer to a single, substantially homogenous acoustic field that sonicates the plurality of sample wells.

11. The sonicator system of claim 1, wherein the multifocus lens layer is configured to focus acoustic energy from the transducer layer to one or more regions that are configured to sonicate the sample array.

12. The sonicator system of claim 1, wherein the multifocus lens layer is configured to focus the acoustic energy from the transducer to an acoustic beam pattern that sonicates the sample array.

13. The sonicator system of claim 1, wherein the multifocus lens layer is configured to focus the acoustic energy of the transducer layer to provide an acoustic field for sonicating the sample array by modifying the phase of the acoustic energy of the transducer layer.

14. The sonicator system of claim 1, wherein materials in the sample array comprise biological samples, chemical sample or combinations thereof.

15. The sonicator system of claim 1, wherein the multifocus acoustic lens layer is configured to focus the acoustic energy so as to shear nucleic acids, proteins, chromatin, intracellular materials or combinations thereof.

16. The sonicator system of claim 1, wherein the multifocus acoustic lens layer is configured to focus the acoustic energy for the lysis of cells, tissue, biofilm or combinations thereof for the extraction or release of intracellular or extracellular materials.

17. The sonicator system of claim 1, wherein the multifocus acoustic lens layer is configured to focus the acoustic energy for in-vitro sonoporation of cells and tissues for the purposes of transfection, drug delivery, or applications requiring a transient permeability of cellular or tissue membrane.

18. The sonicator system of claim 1, further comprising an acoustic matching layer configured to acoustically couple the transducer layer to the multifocus acoustic lens layer.

19. The sonicator system of claim 1, wherein the sample array comprises a microplate.

20. The sonicator system of claim 1, wherein the sample array comprises glass or plastic tubes, containing the materials to be sonicated, and positioned in an array.

21. The sonicator system of claim 1, wherein the multifocus acoustic lens layer is not cylindrically focused.

22. The sonicator system of, claim 1 wherein the multifocus acoustic lens layer produces greater than eight independent acoustic foci.

23. A method of sonicating a plurality of samples in a sample array comprising emitting acoustic energy from the transducer layer and focusing acoustic energy from the transducer layer to a plurality of focal points or regions with the multifocus acoustic lens using the sonicator system of claim 1.

24. A sonicator system for sonicating materials in a sample array, the system comprising:
   a transducer layer configured to emit acoustic energy; and
   a multifocus acoustic lens layer configured to focus the acoustic energy from the transducer layer to the sample array to thereby simultaneously sonicate materials in the sample array, wherein the multifocus lens layer comprises a 3D printed acoustic lens.

25. A method of sonicating a plurality of samples in a sample array, the method comprising:
   emitting acoustic energy from a transducer layer; and
   focusing acoustic energy from the transducer layer to a plurality of focal points or regions with a multifocus acoustic lens to thereby sonicate the plurality of samples in the sample array, wherein the multifocus lens layer is formed by holography techniques.

* * * * *